(12) United States Patent
Starzinski-Powitz et al.

(10) Patent No.: US 6,586,569 B1
(45) Date of Patent: Jul. 1, 2003

(54) ENDOMETRIOSIS-ASSOCIATED GENE

(75) Inventors: Anna Starzinski-Powitz, Zeisselstrasse 9, 60318 Frankfurt (DE); Kotzian Silvia, Hattersheim am Main (DE); Heike Handrow-Metzmacher, Frankfurt am Main (DE)

(73) Assignee: Anna Starzinski-Powitz, Frankfurt (DE)

( * ) Notice: Subject to any disclaimer, the term of this patent is extended or adjusted under 35 U.S.C. 154(b) by 20 days.

(21) Appl. No.: 09/725,311

(22) Filed: Nov. 29, 2000

Related U.S. Application Data

(63) Continuation-in-part of application No. PCT/EP99/03716, filed on May 28, 1999.

(30) Foreign Application Priority Data

May 29, 1998 (DE) .......................................... 198 24 230

(51) Int. Cl.⁷ .............................................. C07K 14/47
(52) U.S. Cl. ...................................... 530/300; 530/350
(58) Field of Search ................................ 530/300, 350, 530/185.1, 192.1

*Primary Examiner*—James Ketter
(74) *Attorney, Agent, or Firm*—Rothwell, Figg, Ernst & Manbeck

(57) ABSTRACT

The invention relates to a gene associated with invasive processes, e.g. endometriosis, to a polypeptide coded by said gene, to an antibody directed against the polypeptide, and to the pharmaceutical application of the nucleic acid, the polypeptide and the antibody.

6 Claims, 1 Drawing Sheet

SEQUENCE LISTING

<160> NUMBER OF SEQ ID NOS: 5

<210> SEQ ID NO 1
<211> LENGTH: 2204
<212> TYPE: DNA
<213> ORGANISM: Homo sapiens
<220> FEATURE:

-continued

```
<221> NAME/KEY: CDS
<222> LOCATION: (3)..(908)

<400> SEQUENCE: 1 cc gcc ctc gtg ccc aag gca gga ctg gcc aag ccc cca gct gct gcc        47
   Ala Leu Val Pro Lys Ala Gly Leu Ala Lys Pro Pro Ala Ala Ala
    1               5                  10                  15 aaa tcc agc cct tcc ctc gcc tct tcg tcc tcg tcc tcg tcc tcc gcg       95
Lys Ser Ser Pro Ser Leu Ala Ser Ser Ser Ser Ser Ser Ser Ser Ala
                 20                  25                  30 gtg gcc ggt ggg gcc ccg gag cag cag gcc ctc ctg agg agg ggc aag      143
Val Ala Gly Gly Ala Pro Glu Gln Gln Ala Leu Leu Arg Arg Gly Lys
             35                  40                  45 agg cac ctg cag ggg gac ggt ctc agc agc ttc gac tcc aga ggc agc      191
Arg His Leu Gln Gly Asp Gly Leu Ser Ser Phe Asp Ser Arg Gly Ser
         50                  55                  60 cgg ccc acc aca gag act gag ttc atc gcc tgg ggg ccc acg ggg gac      239
Arg Pro Thr Thr Glu Thr Glu Phe Ile Ala Trp Gly Pro Thr Gly Asp
     65                  70                  75 gag gag gcc ctg gag tcc aac aca ttt ccg ggc gtt tac ggc ccc acc      287
Glu Glu Ala Leu Glu Ser Asn Thr Phe Pro Gly Val Tyr Gly Pro Thr
 80                  85                  90                  95 acg gtc tcc atc cta caa aca cgg aag aca act gtg gcc gcc acc acc      335
Thr Val Ser Ile Leu Gln Thr Arg Lys Thr Thr Val Ala Ala Thr Thr
                100                 105                 110 acc acc acc acc acg gcc acc ccc atg acg ctg cag act aag ggg ttc      383
Thr Thr Thr Thr Thr Ala Thr Pro Met Thr Leu Gln Thr Lys Gly Phe
            115                 120                 125 acc gag tcc ttg gat ccc cgg aga agg atc cca ggt ggg gtt agc aca      431
Thr Glu Ser Leu Asp Pro Arg Arg Ile Pro Gly Gly Val Ser Thr
        130                 135                 140 acg gag cct tcc acc agt ccc agc aac aac ggg gaa gtc acc cag ccc      479
Thr Glu Pro Ser Thr Ser Pro Ser Asn Asn Gly Glu Val Thr Gln Pro
    145                 150                 155 cca agg att ctg ggg gag gcc tca ggt ctg gct gtc cat cag atc atc      527
Pro Arg Ile Leu Gly Glu Ala Ser Gly Leu Ala Val His Gln Ile Ile
160                 165                 170                 175 acc atc acc gtc tcc ctc atc atg gtc ata gct gct ctc atc aca act      575
Thr Ile Thr Val Ser Leu Ile Met Val Ile Ala Ala Leu Ile Thr Thr
                180                 185                 190 ctt gtc tta aaa aat tgc tgt gcc caa agc ggg aac act cgt cgg aac      623
Leu Val Leu Lys Asn Cys Cys Ala Gln Ser Gly Asn Thr Arg Arg Asn
            195                 200                 205 agc cac cag cgg aag acc aac cag cag gag gag agc tgc cag aac ctc      671
Ser His Gln Arg Lys Thr Asn Gln Gln Glu Glu Ser Cys Gln Asn Leu
        210                 215                 220 acg gac ttc ccc tcg gcc cgg gtg ccc agc agc ctg gac ata ttc acg      719
Thr Asp Phe Pro Ser Ala Arg Val Pro Ser Ser Leu Asp Ile Phe Thr
    225                 230                 235 gcc tat aac gag acc ctg cag tgt tct cac gag tgc gtc agg gca tct      767
Ala Tyr Asn Glu Thr Leu Gln Cys Ser His Glu Cys Val Arg Ala Ser
240                 245                 250                 255 gtg ccc gtg tac acc gat gag acg ctg cac tcg acg acg ggg gag tac      815
Val Pro Val Tyr Thr Asp Glu Thr Leu His Ser Thr Thr Gly Glu Tyr
                260                 265                 270 aaa tcc aca ttt aat gga aac cga ccc tcc tct tct gat cgg cat ctt      863
Lys Ser Thr Phe Asn Gly Asn Arg Pro Ser Ser Ser Asp Arg His Leu
            275                 280                 285 att cct gtg gcc ttc gtg tct gag aaa tgg ttt gaa atc tcc tgc          908
Ile Pro Val Ala Phe Val Ser Glu Lys Trp Phe Glu Ile Ser Cys
```

```
                290               295               300
tgactggccg aagtctttt tacctcctgg gggcaggca gacgccgtgt gtctgtttca    968
cggattccgt tggtgaacct gtaaaaacaa aacaaacaaa acaaaacaaa aaagacaaaa  1028
cctaaaactg agctatctaa gggggagggt ccccgcacct accacttctg tttgccggtg  1088
ggaaactcac agagcaggac gctctaggcc aaatctattt ttgtaaaaat gctcatgcct  1148
atgggtgact gccttctccc agagttttct ttggagaaca gaaagaagaa aggaaagaaa  1208
ggaaccagag gcagagagac gaggatacccc agcgaaaggg acgggaggaa gcatccgaaa  1268
cctaggattc gtcctacgat tctgaacctg tgccaataat accattatgt gccatgtact  1328
gacccgaaag gctcggccac agagccgggg cccagcgaat cacgcagaga atcttacag   1388
aaaacagggg tgggaatctc ttccgataga gtcgctattt ctggttaata tacatatata  1448
aatatataaa tacaaacaca cacacacact ttttttgtac tgtagcaatt tttgaagatc  1508
ttaaatgttc ctttttaaaa aaaagaattg tgttataggt tacaaaatct gatttattta  1568
acatgcttag tatgagcaga ataaaccagt gttttctact ttggcaactc acgtcacaca  1628
catattacac acatgtgcgc atacacacac acaatacaca tatatgcata tagacgcatc  1688
tattggaaat gcagttccac aggtgagcat gttctttctg gtgacctggt attccatcac  1748
cattcaccccc aggggacagc ctcgaccgag acaaggaggc ccttaaatga cagcctgcat  1808
ttgctagacg gttggtgagt ggcatcaaat gtgtgactta ctatcttggg ccagaactaa  1868
gaatgccaag gttttatata tgtgtgtata tatatatata tatatatata tatatgtttg  1928
tgtgtgtata tatatatata tatatatatg tttgtgtgtg tatatatatg tttgtgtata  1988
tatatacaca tatgcataca tatgattttt ttttttttcat ttaagtgttg gaagatgcta  2048
cctaacagcc acgttcacat ttacgtagct ggttgcttac aaacgggcct gagcccctgg  2108
ttgggtgggt ggtggattct tggacgtgtg tgtcatacaa gcatagactg gattaaagaa  2168
gttttccagt tccaaaaatt aaaggaatat atcctt                            2204
```

<210> SEQ ID NO 2
<211> LENGTH: 302
<212> TYPE: PRT
<213> ORGANISM: Homo sapiens

<400> SEQUENCE: 2

```
Ala Leu Val Pro Lys Ala Gly Leu Ala Lys Pro Pro Ala Ala Ala Lys
 1               5                  10                  15

Ser Ser Pro Ser Leu Ala Ser Ser Ser Ser Ser Ser Ser Ser Ala Val
            20                  25                  30

Ala Gly Gly Ala Pro Glu Gln Gln Ala Leu Leu Arg Arg Gly Lys Arg
        35                  40                  45

His Leu Gln Gly Asp Gly Leu Ser Ser Phe Asp Ser Arg Gly Ser Arg
    50                  55                  60

Pro Thr Thr Glu Thr Glu Phe Ile Ala Trp Gly Pro Thr Gly Asp Glu
65                  70                  75                  80

Glu Ala Leu Glu Ser Asn Thr Phe Pro Gly Val Tyr Gly Pro Thr Thr
                85                  90                  95

Val Ser Ile Leu Gln Thr Arg Lys Thr Thr Val Ala Ala Thr Thr Thr
            100                 105                 110

Thr Thr Thr Thr Ala Thr Pro Met Thr Leu Gln Thr Lys Gly Phe Thr
        115                 120                 125

Glu Ser Leu Asp Pro Arg Arg Arg Ile Pro Gly Gly Val Ser Thr Thr
```

-continued

```
              130                 135                 140
Glu Pro Ser Thr Ser Pro Ser Asn Asn Gly Glu Val Thr Gln Pro Pro
145                 150                 155                 160

Arg Ile Leu Gly Glu Ala Ser Gly Leu Ala Val His Gln Ile Ile Thr
                165                 170                 175

Ile Thr Val Ser Leu Ile Met Val Ile Ala Ala Leu Ile Thr Thr Leu
                180                 185                 190

Val Leu Lys Asn Cys Cys Ala Gln Ser Gly Asn Thr Arg Arg Asn Ser
                195                 200                 205

His Gln Arg Lys Thr Asn Gln Gln Glu Glu Ser Cys Gln Asn Leu Thr
                210                 215                 220

Asp Phe Pro Ser Ala Arg Val Pro Ser Ser Leu Asp Ile Phe Thr Ala
225                 230                 235                 240

Tyr Asn Glu Thr Leu Gln Cys Ser His Glu Cys Val Arg Ala Ser Val
                245                 250                 255

Pro Val Tyr Thr Asp Glu Thr Leu His Ser Thr Thr Gly Glu Tyr Lys
                260                 265                 270

Ser Thr Phe Asn Gly Asn Arg Pro Ser Ser Ser Asp Arg His Leu Ile
                275                 280                 285

Pro Val Ala Phe Val Ser Glu Lys Trp Phe Glu Ile Ser Cys
                290                 295                 300

<210> SEQ ID NO 3
<211> LENGTH: 2288
<212> TYPE: DNA
<213> ORGANISM: Homo sapiens
<220> FEATURE:
<221> NAME/KEY: CDS
<222> LOCATION: (3)..(992)

<400> SEQUENCE: 3 cc cgg ccg ccc cga gtg gag cgg atc cac ggg cag atg cag atg cct        47
   Arg Pro Pro Arg Val Glu Arg Ile His Gly Gln Met Gln Met Pro
     1               5                  10                  15 cga gcc aga cgg gcc cac agg ccc cgg gac cag gcg gcc gcc ctc gtg       95
Arg Ala Arg Arg Ala His Arg Pro Arg Asp Gln Ala Ala Ala Leu Val
                20                  25                  30 ccc aag gca gga ctg gcc aag ccc cca gct gct gcc aaa tcc agc cct      143
Pro Lys Ala Gly Leu Ala Lys Pro Pro Ala Ala Ala Lys Ser Ser Pro
            35                  40                  45 tcc ctc gcc tct tcg tcc tcg tcc tcg tcc tcc gcg gtg gcc ggt ggg      191
Ser Leu Ala Ser Ser Ser Ser Ser Ser Ser Ser Ala Val Ala Gly Gly
        50                  55                  60 gcc ccg gag cag cag gcc ctc ctg agg agg ggc aag agg cac ctg cag      239
Ala Pro Glu Gln Gln Ala Leu Leu Arg Arg Gly Lys Arg His Leu Gln
    65                  70                  75 ggg gac ggt ctc agc agc ttc gac tcc aga ggc agc cgg ccc acc aca      287
Gly Asp Gly Leu Ser Ser Phe Asp Ser Arg Gly Ser Arg Pro Thr Thr
80                  85                  90                  95 gag act gag ttc atc gcc tgg ggg ccc acg ggg gac gag gag gcc ctg      335
Glu Thr Glu Phe Ile Ala Trp Gly Pro Thr Gly Asp Glu Glu Ala Leu
                100                 105                 110 gag tcc aac aca ttt ccg ggc gtt tac ggc ccc acc acg gtc tcc atc      383
Glu Ser Asn Thr Phe Pro Gly Val Tyr Gly Pro Thr Thr Val Ser Ile
            115                 120                 125 cta caa aca cgg aag aca act gtg gcc gcc acc acc acc acc acc          431
Leu Gln Thr Arg Lys Thr Thr Val Ala Ala Thr Thr Thr Thr Thr
        130                 135                 140
```

| | |
|---|---|
| acg gcc acc ccc atg acg ctg cag act aag ggg ttc acc gag tcc ttg<br>Thr Ala Thr Pro Met Thr Leu Gln Thr Lys Gly Phe Thr Glu Ser Leu<br>145 150 155 | 479 |
| gat ccc cgg aga agg atc cca ggt ggg gtt agc aca acg gag cct tcc<br>Asp Pro Arg Arg Arg Ile Pro Gly Gly Val Ser Thr Thr Glu Pro Ser<br>160 165 170 175 | 527 |
| acc agt ccc agc aac aac ggg gaa gtc acc cag ccc cca agg att ctg<br>Thr Ser Pro Ser Asn Asn Gly Glu Val Thr Gln Pro Pro Arg Ile Leu<br>180 185 190 | 575 |
| ggg gag gcc tca ggt ctg gct gtc cat cag atc atc acc atc acc gtc<br>Gly Glu Ala Ser Gly Leu Ala Val His Gln Ile Ile Thr Ile Thr Val<br>195 200 205 | 623 |
| tcc ctc atc atg gtc ata gct gct ctc atc aca act ctt gtc tta aaa<br>Ser Leu Ile Met Val Ile Ala Ala Leu Ile Thr Thr Leu Val Leu Lys<br>210 215 220 | 671 |
| aat tgc tgt gcc caa agc ggg aac act cgt cgg aac agc cac cag cgg<br>Asn Cys Cys Ala Gln Ser Gly Asn Thr Arg Arg Asn Ser His Gln Arg<br>225 230 235 | 719 |
| aag acc aac cag cag gag gag agc tgc cag aac ctc acg gac ttc ccc<br>Lys Thr Asn Gln Gln Glu Glu Ser Cys Gln Asn Leu Thr Asp Phe Pro<br>240 245 250 255 | 767 |
| tcg gcc cgg gtg ccc agc agc ctg gac ata ttc acg gcc tat aac gag<br>Ser Ala Arg Val Pro Ser Ser Leu Asp Ile Phe Thr Ala Tyr Asn Glu<br>260 265 270 | 815 |
| acc ctg cag tgt tct cac gag tgc gtc agg gca tct gtg ccc gtg tac<br>Thr Leu Gln Cys Ser His Glu Cys Val Arg Ala Ser Val Pro Val Tyr<br>275 280 285 | 863 |
| acc gat gag acg ctg cac tcg acg acg ggg gag tac aaa tcc aca ttt<br>Thr Asp Glu Thr Leu His Ser Thr Thr Gly Glu Tyr Lys Ser Thr Phe<br>290 295 300 | 911 |
| aat gga aac cga ccc tcc tct tct gat cgg cat ctt att cct gtg gcc<br>Asn Gly Asn Arg Pro Ser Ser Ser Asp Arg His Leu Ile Pro Val Ala<br>305 310 315 | 959 |
| ttc gtg tct gag aaa tgg ttt gaa atc tcc tgc tgactggccg aagtctttt<br>Phe Val Ser Glu Lys Trp Phe Glu Ile Ser Cys<br>320 325 330 | 1012 |
| tacctcctgg gggcagggca gacgccgtgt gtctgtttca cggattccgt tggtgaacct | 1072 |
| gtaaaaacaa aacaaacaaa acaaaacaaa aaagacaaaa cctaaaactg agctatctaa | 1132 |
| gggggagggt ccccgcacct accacttctg tttgccggtg ggaaactcac agagcaggac | 1192 |
| gctctaggcc aaatctattt ttgtaaaaat gctcatgcct atgggtgact gccttctccc | 1252 |
| agagttttct ttggagaaca gaaagaagaa aggaaagaaa ggaaccagag gcagagagac | 1312 |
| gaggataccc agcgaaaggg acgggaggaa gcatccgaaa cctaggattc gtcctacgat | 1372 |
| tctgaacctg tgccaataat accattatgt gccatgtact gaccccgaaag gctcggccac | 1432 |
| agagccgggg cccagcgaat cacgcagaga aatcttacag aaaacagggg tgggaatctc | 1492 |
| ttccgataga gtcgctattt ctggttaata tacatatata aatatataaa tacaaacaca | 1552 |
| cacacacact ttttttgtac tgtagcaatt tttgaagatc ttaaatgttc cttttttaaa | 1612 |
| aaaagaattg tgttataggt tacaaaatct gatttattta acatgcttag tatgagcaga | 1672 |
| ataaaccagt gtttttctact ttggcaactc acgtcacaca catattacac acatgtgcgc | 1732 |
| atacacacac acaatacaca tatatgcata tagacgcatc tattggaaat gcagttccac | 1792 |
| aggtgagcat gttctttctg gtgacctggt attccatcac cattcacccc aggggacagc | 1852 |
| ctcgaccgag acaaggaggc ccttaaatga cagcctgcat ttgctagacg gttggtgagt | 1912 |
| ggcatcaaat gtgtgactta ctatcttggg ccagaactaa gaatgccaag gttttatata | 1972 |

```
tgtgtgtata tatatatata tatatatata tatatgtttg tgtgtgtata tatatatata    2032
tatatatatg tttgtgtgtg tatatatatg tttgtgtata tatatacaca tatgcataca    2092 tatgatttt ttttttttcat ttaagtgttg gaagatgcta cctaacagcc acgttcacat    2152
ttacgtagct ggttgcttac aaacgggcct gagcccctgg ttgggtgggt ggtggattct    2212
tggacgtgtg tgtcatacaa gcatagactg gattaaagaa gttttccagt tccaaaaatt    2272
aaaggaatat atcctt                                                    2288
```

<210> SEQ ID NO 4
<211> LENGTH: 330
<212> TYPE: PRT
<213> ORGANISM: Homo sapiens

<400> SEQUENCE: 4

```
Arg Pro Pro Arg Val Glu Arg Ile His Gly Gln Met Gln Met Pro Arg
 1               5                  10                  15

Ala Arg Arg Ala His Arg Pro Arg Asp Gln Ala Ala Ala Leu Val Pro
             20                  25                  30

Lys Ala Gly Leu Ala Lys Pro Ala Ala Ala Lys Ser Ser Pro Ser
         35                  40                  45

Leu Ala Ser Ser Ser Ser Ser Ser Ala Val Ala Gly Gly Ala
     50                  55                  60

Pro Glu Gln Gln Ala Leu Leu Arg Arg Gly Lys Arg His Leu Gln Gly
 65                  70                  75                  80

Asp Gly Leu Ser Ser Phe Asp Ser Arg Gly Ser Arg Pro Thr Thr Glu
                 85                  90                  95

Thr Glu Phe Ile Ala Trp Gly Pro Thr Gly Asp Glu Glu Ala Leu Glu
            100                 105                 110

Ser Asn Thr Phe Pro Gly Val Tyr Gly Pro Thr Thr Val Ser Ile Leu
        115                 120                 125

Gln Thr Arg Lys Thr Thr Val Ala Ala Thr Thr Thr Thr Thr Thr Thr
    130                 135                 140

Ala Thr Pro Met Thr Leu Gln Thr Lys Gly Phe Thr Glu Ser Leu Asp
145                 150                 155                 160

Pro Arg Arg Arg Ile Pro Gly Gly Val Ser Thr Thr Glu Pro Ser Thr
                165                 170                 175

Ser Pro Ser Asn Asn Gly Glu Val Thr Gln Pro Pro Arg Ile Leu Gly
            180                 185                 190

Glu Ala Ser Gly Leu Ala Val His Gln Ile Ile Thr Ile Thr Val Ser
        195                 200                 205

Leu Ile Met Val Ile Ala Ala Leu Ile Thr Thr Leu Val Leu Lys Asn
    210                 215                 220

Cys Cys Ala Gln Ser Gly Asn Thr Arg Arg Asn Ser His Gln Arg Lys
225                 230                 235                 240

Thr Asn Gln Gln Glu Glu Ser Cys Gln Asn Leu Thr Asp Phe Pro Ser
                245                 250                 255

Ala Arg Val Pro Ser Ser Leu Asp Ile Phe Thr Ala Tyr Asn Glu Thr
            260                 265                 270

Leu Gln Cys Ser His Glu Cys Val Arg Ala Ser Val Pro Val Tyr Thr
        275                 280                 285

Asp Glu Thr Leu His Ser Thr Thr Gly Glu Tyr Lys Ser Thr Phe Asn
    290                 295                 300

Gly Asn Arg Pro Ser Ser Ser Asp Arg His Leu Ile Pro Val Ala Phe
```

```
305                 310                 315                 320
Val Ser Glu Lys Trp Phe Glu Ile Ser Cys
                325                 330

<210> SEQ ID NO 5
<211> LENGTH: 218
<212> TYPE: DNA
<213> ORGANISM: Homo sapiens

<400> SEQUENCE: 5
gcggttgtcc ggaatgccag tggctcctgg gcagatgtgc accccagatt cagcctttgt     60
gatagattcc aacacgttct ggcctcagac cacctttgtg gtggggccag actgctctgg   120
gcaaagtgaa gctggccttt atgctccaag gaaggggggcc tcgagagcag gcctgcattg   180
gctctcggac taattcgcga tcatctttca tacagcag                            218
```

ENDOMETRIOSIS-ASSOCIATED GENE

CROSS REFERENCE TO RELATED APPLICATION

Figure 1:
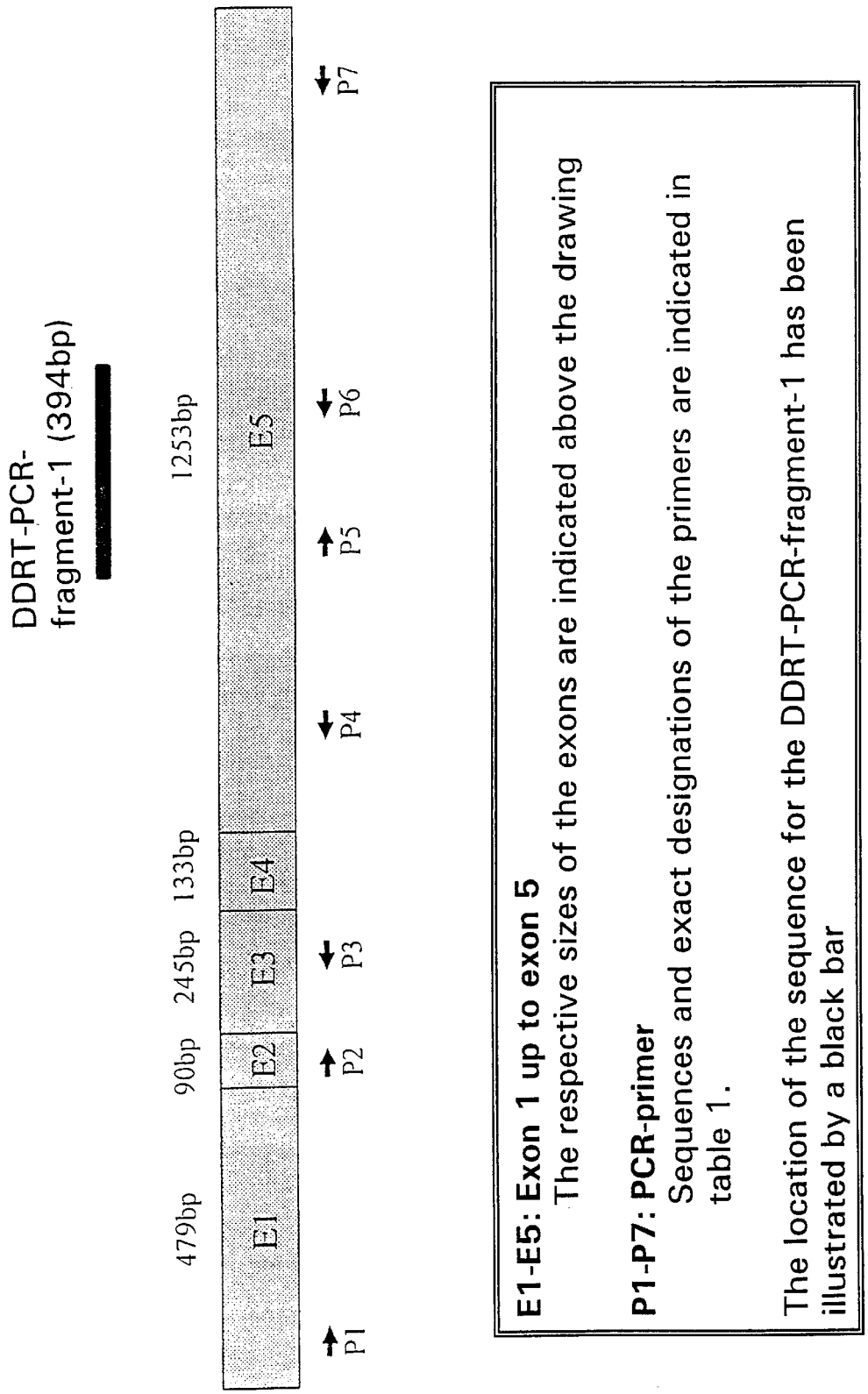

This application is a. continuation-in-part of International Application PCT/EP99/03716, filed May 28, 1999, and designating the U.S.

DESCRIPTION

The present invention relates to a gene associated with invasive processes, for example endometriosis, to a polypeptide encoded by it, to an antibody directed against the polypeptide, and to the pharmaceutical application of the nucleic acid, the polypeptide and the antibody.

Endometriosis is the second most common disease in women and is defined as the occurrence of endometrial cells outside the womb. Endometriosis affects about one in five women of reproductive age, and as many as one in two women with fertility problems.

In normal circumstances the endometrium is only found in the womb. In endometriosis, tissue with a histological appearance resembling the endometrium is found outside the womb, for example externally on the womb, on the intestine or even in the pancreas or the lung. Although these endometriotic foci are located outside the womb, they also bleed during menstruation, thus they are influenced by hormones of the female cycle. Since endometriotic foci like the endometrium go through volume changes during the cycle, these changes may cause pain depending on location. Moreover, the body reacts to endometriotic cells with an inflammatory response which again causes pain. Furthermore, inflammation leads to adhesions in the area of the ovaries and fallopian tubes and, as a result of these, is responsible for a so-called mechanical sterility of affected women. Apparently however, in endometriosis messengers are released as well (e.g. cytokines, prostaglandins) which can reduce the fertility of affected women even in the absence of adhesions.

In view of their pathobiological properties, endometriotic cells could be classified as being between normal cells and tumor cells: on the one hand they show no neoplastic behavior, on the other hand, however, they are, like metastasizing tumor cells, capable of moving across organ boundaries in the organism and of growing into other organs, i.e. they show invasive behavior. For this reason endometriotic cells are defined as "benign tumor cells" in the literature, although up until now no tumor-specific-mutations in proto-oncogenes have been found in cells of this type.

Since the pathogenesis of endometriosis is still not clarified completely, there are as yet no effective options for the therapy or prevention of endometriosis-associated diseases.

It was the object of the invention to identify novel genes which play a role in invasive processes and which may be associated with the pathophysiological phenotype of endometriosis.

This object is achieved according to the invention by identifying, cloning and characterizing a gene which is called an endometriosis-associated gene and which codes for a polypeptide. This gene sequence was discovered with the aid of differential display RT-PCR (Liang and Pardee, Science 257 (1992), 967–971). For this, invasive and noninvasive variants of an endometriotic cell line were compared with each other. In the process a cDNA sequence was found which is specific for the invasive variant of endometriotic cells. An associated RNA of 4 kb in length was found. A corresponding cDNA isolated from a cDNA phage bank has an open reading frame (ORF) of 302 amino acids.

The present invention relates to a nucleic acid which comprises (a) the nucleotide sequences depicted in SEQ ID NO. 1, 3 or/and 5, a combination or a protein-encoding segment thereof, (b) a nucleotide sequence corresponding to the sequence in (a) within the scope of the degeneracy of the genetic code or (c) a nucleotide sequence hybridizing with the sequences in (a) and/or (b) under stringent conditions.

The nucleic acids preferably code for a polypeptide associated with invasive processes or a segment thereof.

The following nucleotide sequences have been deposited in the EMBL EST database with the following accession numbers: Z98886, Ac003017, AL023586, Aa52993, Aa452856. These sequences do not represent nucleic acids according to the invention. The first two of these sequences are DNAs which were isolated from human brain and show over 90% identical bases to SEQ. ID NO. 1 in the segments from nucleotide 970 to about 2000 and from 760 to about 1450, respectively, or in the segments from nucleotide 1054 to 2084 and from 844 to about 1534 in relation to SEQ ID NO. 3 which has 84 additional bases at the 5' end. AL023586 is also a human sequence which is very similar to Z98885 and also has homology with SEQ ID NO. 1 in the region from 970 to about 2000.

Sequences Aa452993 and Aa452856 originate from mouse embryos and show base identity with the nucleotides (nt) from about 1060 to about 1450 and from about 24 to 440, respectively, of SEQ. ID NO. 1, or from about 1144 to about 1534 and from about 108 to about 524, respectively, according to the nucleotide positions in SEQ. ID NO. 3. Up until now no reading frame or function has been assigned to any of these 4 sequences.

The nucleotide sequence depicted in SEQ. ID NO. 1 contains an open reading frame which corresponds to a polypeptide having a length of 302 amino acids. This polypeptide is indicated in the amino acid sequence depicted SEQ. ID NO. 2. SEQ. ID NO. 3 shows a nucleotide sequence as in SEQ. ID NO. 1, but it has 84 additional nucleotides at the 5' end. As a result, the positions of the nucleotides corresponding to each other shift by 84 nucleotides in each case. The polypeptide encoded by SEQ. ID NO. 3 therefore has 28 additional amino acids at the N terminus and is depicted in SEQ. ID NO. 4 with its total of 330 amino acids. SEQ. ID NO. 2 and 4 depict a C-terminal segment of the native polypeptide.

For illustration purposes reference is made to FIG. 1 which shows a diagrammatic representation of the cDNA of the endometriosis-associated gene according to the invention. Five exons, E1 to E5, and the position of fragment 1 (394 nt) used as a probe in DDRT-PCR are shown. The positions of the PCR primers (see example 4, table 1) used for RT-PCR are also shown.

Not shown in FIG. 1 is a further exon 4a whose nucleotide sequence is shown in SEQ. ID NO. 5. This exon 4a may be present. If it is present, it is found between exon 4 and exon 5. This corresponds to the position between nt1054 and nt1055 in SEQ. ID NO. 3. A combination of the sequences SEQ. ID NO. 1/3 with SEQ. ID NO. 5 is accordingly, for example, a sequence which contains the sequence of the exon 4a at said position.

Besides the nucleotide sequences shown in SEQ. ID NO. 1, 3 and 5 and combinations thereof such as the sequence of SEQ. ID NO. 3, which has the sequence of SEQ. ID NO. 5 between nt1054 and 1055 and to a nucleotide sequences which corresponds to the sequences within the scope of the degeneracy of the genetic code, the present invention also includes nucleotide sequences which hybridize with one of the sequences mentioned before. The term "hybridization" according to the present invention is used by Sambrook et al. (Molecular Cloning, A Laboratory Manual, Cold Spring Harbor Laboratory Press (1989), 1.101–1.104). Preferably a hybridization is called stringent if a positive hybridization signal is still observed after washing for one hour with 1×SSC and 0.1% SDS at 50° C., preferably at 55° C., particularly preferably at 62° C. and most preferably at 68° C., in particular for 1 h in 0.2×SSC and 0.1% SDS at 55° C., preferably at 55° C., particularly preferably at 62° C. and most preferably at 68° C. A nucleotide sequence hybridizing under these washing conditions with one or more of the nucleotide sequences depicted in SEQ ID NO. 1, 3 and 5, or with a nucleic sequence corresponding to these sequences within the scope of the degeneracy of the genetic code, is a nucleotide sequence according to the invention.

The nucleotide sequence according to the invention is preferably a DNA. However, it can also include an RNA or a nucleic acid analog such as a peptidic nucleic acid, for example. Particularly preferably the nucleic acid according to the invention includes a protein-encoding segment of the nucleotide sequences depicted in SEQ ID NO. 1, 3 and/or 5 or a sequence having a homology of more than 80%, preferably more than 90% and particularly preferably more than 95% to the nucleotide sequences depicted in SEQ ID NO. 1, 3 or 5 or a segment of preferably at least 20 nucleotides (nt) and particularly preferably at least 50 nt thereof. The same also holds for nucleic acids which have, as described above, the sequence of SEQ. ID NO. 5 in addition to those of SEQ ID NO. 1 or 3. The homology is given in percent identical positions when two nucleic acids (or peptide chains) are compared, where a 100% homology means complete identity of the compared chain molecules (Herder: Lexikon der Biochemie und Molekularbiologie [Dictionary of biochemistry and molecular biology], Spektrum Akademischer Verlag 1995).

Nucleic acids according to the invention are preferably obtainable from mammals and in particular from humans. They may be isolated according to known techniques by using short segments of the nucleotide sequences shown in SEQ. ID NO. 1, 3 or/and 5 as hybridization probes and/or as amplification primers. Furthermore, the nucleic acids according to the invention may also be prepared by chemical synthesis, it being possible to employ modified nucleotide building blocks, for example 2'-O-alkylated nucleotide building blocks, where appropriate, instead of conventional nucleotide building blocks.

The nucleic acids according to the invention or segments thereof may therefore be used for preparing primers and probes which preferably contain markers or labeling groups. Preference is also given to intron-bridging oligonucleotide primers which are particularly suitable for identifying different mRNA species.

The present invention further relates to polypeptides encoded by the nucleic acids defined as above. These polypeptides preferably comprise (a) the amino acid sequence depicted in SEQ ID NO. 2 or 4 or (b) a homology of more than 70%, preferably of more than 80% and particularly preferably of more than 90% to the amino acid sequence according to (a).

Besides the polypeptides depicted in SEQ ID NO. 2 or 4, the invention also relates to muteins, variants and fragments thereof. These are sequences which differ from the amino acid sequences depicted in SEQ ID NO. 2 or 4 by substitution, deletion and/or insertion of single amino acids or of short amino acid segments.

The term "variant" includes both naturally occurring allelic variations or splicing variations of the endometriotic protein, and proteins generated by recombinant DNA technology (in particular in vitro mutagenesis with the aid of chemically synthesised oligonucleotides) which correspond substantially to the proteins depicted in SEQ ID NO. 2 or 4 with respect to their biological and/or immunological activity. This term also includes chemically modified polypeptides. Polypeptides which are modified at the termini and/or in the reactive amino acid side groups by acylation, for example acetylation or amidation belong to this group. Polypeptide fragments (peptides) representing a segment of at least 10 amino acids of the amino acid sequence shown in SEQ ID NO. 2 or 4 also belong to the amino acid sequences according to the invention.

The present invention further relates to a vector containing at least one copy of a nucleic acid according to the invention. This vector may be any prokaryotic or eukaryotic vector on which the DNA sequence according to the invention, preferably linked to expression signals such as promoter, operator, enhancer etc., is located. Examples of prokaryotic vectors are chromosomal vectors such as bacteriophages and extrachromosomal vectors such as plasmids, with circular plasmid vectors being particularly preferred. Suitable prokaryotic vectors are described, for example, in Sambrook et al., supra, Chapters 1–4. Particularly preferred is the vector according to the invention, a eukaryotic vector, e.g. a yeast vector, or a vector suitable for higher cells, e.g. plasmid vector, viral vector or plant vector. Vectors of this type are well known to the skilled worker in the field of molecular biology so that there is no need for further explanation here. In particular, reference is made in this connection to Sambrook et al., supra, Chapter 16.

The invention also relates to a vector which contains a segment of at least 21 nucleotides in length of the sequences depicted in SEQ ID NO. 1, 3 or/and 5 or a combination thereof. Preferably this segment has a nucleotide sequence which originates from the protein-encoding region of said sequences or from a region essential for the expression of the protein or polypeptide. These nucleic acids are particularly suitable for preparing therapeutically employable antisense nucleic acids preferably of up to 50 nucleotides in length.

The present invention further relates to a cell. transformed with a nucleic acid according to the invention or a vector according to the invention. The cell can be both a eukaryotic and a prokaryotic cell. Methods for transforming cells with nucleic acids are general prior art and therefore need no further explanation. Examples of preferred cells are eukaryotic cells, in particular animal and particularly preferably mammalian cells.

The present invention further relates to an antibody or a fragment of such an antibody against the polypeptide(s) encoded by the endometriosis gene or against variants thereof. Antibodies of this type are particularly preferably directed against complete polypeptides encoded by it or against a peptide sequence corresponding to amino acids 1–330 of the amino acid sequence depicted in SEQ ID NO. 4.

Identification, isolation and expression of a gene according to the invention which is specifically associated with invasive processes and in particular with endometriosis provide the requirements for diagnosis, therapy and prevention of diseases based on those disorders mentioned above.

It becomes possible with the aid of a polypeptide according to the invention or fragments of this polypeptide as immunogen to prepare antibodies against those polypeptides. Preparation of antibodies may be carried out in the usual way by immunizing experimental animals with the complete polypeptide or fragments thereof and subsequently obtaining the resulting polyclonal antisera. According to the method of Köhler and Milstein and its developments monoclonal antibodies can be obtained from the antibody-producing cells of the experimental animals by cell fusion in the known manner. In the same way, human monoclonal antibodies can be produced according to known methods. Antibodies of this type could then be used both for diagnostic tests, in particular of endometriotic cell tissue, or else for the therapy.

For example, samples such as body fluids, in particular human body fluids (e.g. blood, lymph or CSF) may be tested with the aid of the ELISA technique on the one hand for the presence of a polypeptide encoded by the endometriosis gene, on the other hand for the presence of autoantibodies against such a polypeptide. Polypeptides encoded by the endometriosis gene or fragments thereof can then be detected in such samples with the aid of a specific antibody, for example of an antibody according to the invention. For detecting autoantibodies it is preferably possible to employ recombinant fusion proteins which contain a part or a domain or even the complete polypeptide encoded by the endometriosis gene and which are fused to a protein domain which facilitates detection, for example maltose-binding protein (MBP).

Diagnostic tests may also be carried out with the aid of specific nucleic acid probes for detecting at the nucleic acid level, for example at the gene or transcript level.

Provision of the nucleotide and amino acid sequences and antibodies according to the invention further facilitates a targeted search for effectors of the polypeptides/proteins. Effectors are agents which act in an inhibitory or activating manner on the polypeptide according to the invention and which are capable of selectively influencing cell functions controlled by the polypeptides. These may then be employed in the therapy of appropriate pathologies, such as those based on invasive processes. The invention therefore also relates to a method for identifying effectors of endometriotic proteins where cells expressing the protein are brought into contact with various potential effector substances, for example low molecular weight agents, and the cells are analyzed for modifications, for example cell-activating, cell-inhibiting, cell-proliferative and/or cell-genetic modifications. In this way it is also possible to identify binding targets of endometriotic proteins.

Since many neoplastic diseases are accompanied by invasive processes, the discovery of the gene according to the invention additionally provides possibilities for the diagnosis, prevention and therapy of cancerous diseases.

The discovery of a gene involved in the responsibility for invasive processes not only opens up possibilities for the treatment of diseases based on cellular modifications of this type, but the sequences according to the invention may also be used in order to make such processes usable. This can be of importance, for example, for the implantation of embryos.

The present invention therefore also relates to a pharmaceutical composition which includes as active components nucleic acids, vectors, cells, polypeptides, peptides and/or antibodies, as mentioned before.

The pharmaceutical composition according to the invention may further contain pharmaceutically conventional carriers, excipients and/or additives and, where appropriate, further active components. The pharmaceutical composition may be employed in particular for the diagnosis, therapy or prevention of diseases associated with invasive processes. Furthermore the composition according to the invention may also be employed for diagnosing a predisposition for such diseases, in particular for diagnosing an endometriosis risk.

The invention is illustrated in more detail by the following figures, sequence listings and examples.

FIG. 1 shows a diagrammatic representation of the cDNA of the endometriosis-associated gene where only exons E1 to E5 are shown.

SEQ ID NO. 1 represents a nucleotide sequence which contains genetic information coding for the endometriosis-associated gene, where an open reading frame extends from nucleotide 3 to 911, and SEQ ID NO. 2 represents the amino acid sequence of the open reading frame of the nucleotide sequence shown in SEQ ID NO. 1, where the amino acid sequence of the open reading frame extends from amino acid 1 to 302.

SEQ ID NO. 3 represents a nucleotide sequence like that of SEQ ID NO. 1 but it contains an additional 84 nucleotides at the 5' end, the open reading frame extends from nucleotide 3 to 995.

SEQ ID NO. 4 represents the amino acid sequence of the open reading frame of the nucleotide sequence shown in SEQ ID NO. 3, where this amino acid sequence has 320 amino acids of which the C-terminal 302 are identical to those in SEQ ID NO. 2.

SEQ ID NO. 5 represents of the nucleotide sequence of the possibly present additional exon 4a consisting of the 218 nt shown, where exon 4a, if it is present, is located between nucleotide 1054 and 1055 (in relation to SEQ ID NO. 3).

EXAMPLES

Example 1

Cell Culturing

To identify an endometriosis-associated gene, invasive and noninvasive cells of the epithelial endometriotic cell line EEC145T$^+$ were used. The cells were cultured in Dulbecco's medium (DMEM) with 10% fetal calf serum and diluted 1:5 2× per week (passage). For comparison of the expression patterns by means of DDRT-PCR (see below) invasive cells of passage 17 and noninvasive cells of passage 33 were used. The cells were transformed with SV40 and analyzed by differential display reverse transcription polymerase chain reaction (DDRT-PCR).

Example 2

DDRT-PCR

This method developed by Liang and Pardee is a method for distinguishing expression patterns of different cell types or the alteration in the expression pattern of one cell type under different living conditions or during altering stages of development (Liang and Pardee (1992), Science 257, 967–971). The basis of the DDRT-PCR technique is based on the idea that in each cell about 15,000 genes are expressed and that in principle each individual mRNA molecule can be prepared by means of reverse transcription and amplification with random primers.

In this example the cellular polyA$^+$ RNA was initially transcribed into cDNA with the aid of several different dT$_{11}$VX primers (downstream primers, anchor primers). The resulting cDNA populations were then PCR-amplified using 4 downstream and 20 upstream primers from the RNA Map™ Kit from Genhunter, Nashville. (1994), with the addition of a radiolabeled nucleotide. After the amplification the reaction mixtures were concentrated in vacuo and the obtained cDNA fragments were fractionated in a six-percent native PAA (polyacrylamide) gel. DNA detection was carried out by autoradiography. PCR mixtures showing distinct differences in the band pattern for the two cell variants to be studied were repeated twice in order to test reproducibility. If the previously found differences were confirmed, the bands were eluted from the gel according to known methods, reamplified, cloned and sequenced.

By this method a 394 bp fragment (fragment 1, nucleotides 1235 to 1628 of the nucleic acid sequence depicted in SEQ ID NO. 1, see also FIG. 1) was found which was specific for the invasive cell variant. This fragment 1 was used as a probe in Northern blot analysis (see below).

Example 3

Analysis of the Fragment 1 Expression Profile in Human Northern Blot Analyses

To test the expression pattern for DDRT-PCR fragment 1, Northern blot analyses were carried out. For this 20 μg of total RNA or 4 μg of polyA+ RNA were fractionated in 1% denaturating agarose gels and transferred onto a nylon membrane overnight. The RNA was fixed to the membrane by irradiation with UV light. Hybridization with $^{32}$P-labeled probes (labeling by means of RPL kit from Amersham) took place overnight in a formamide-containing hybridization solution at 42° C. Subsequently the membrane was washed under increasing stringency until the spots of radioactive emission were of measurable intensity. The hybridization pattern was visualized by putting on an X-ray film (NEF-NEN, DuPont) and exposing over several days. To determine the expression pattern for DDRT-PCR fragment 1, Northern blot analyses were carried out using RNA from the following cells or tissues:

invasive cells of the epithelial endometriotic cell line EEC145T$^+$ (passage 17)
noninvasive cells of the epithelial endometriotic cell line EEC145T$^+$ (passage 33)
cells of the peritoneal cell line EEC143T$^+$
endometrial tissue
cells of the invasive human bladder carcinoma cell line EJ28
cells of the noninvasive human bladder carcinoma cell line RT112

After hybridization with the probe for DDRT-PCR fragment 1 an mRNA of about 4 kb was detectable, and it was exclusively detectable in the invasive variant of the endometriotic cell line EEC145T$^+$.

Further human tissues were tested. In the spleen an mRNA of 4 kb in length was found which hybridized unambiguously with fragment 1, and in brain mRNAs of 4 kb and >9 kb in length, respectively, were found.

Northern blot analyses were carried out according to the manufacturer's protocol using two human multiple tissue Northern (MTN) blots from Clontech. Expression was tested in the following tissues: colon, small intestine, heart, brain, testicles, liver, lung, spleen, kidney, ovaries, pancreas, peripheral blood leukocytes, placenta, prostate, skeletal muscle, thymus. The expression pattern obtained using the radiolabeled 3' probe "DDRT-PCR fragment 1" appears as follows:

4 kb mRNA (expected size):
  brain,
  spleen,
  pancreas
9.5 kb mRNA:
  brain

In the remaining tissues no specific hybridization was detectable.

In-situ hybridization

To elucidate the cellular expression pattern, mRNA in-situ hybridizations were carried out on 10 μm paraffin sections of different tissues. For this the "DDRT-PCR fragment 1" was employed as digoxigenin-labeled RNA probe. The detection reaction was carried out by means of a digoxigenin-specific antibody coupled to alkaline phosphatase (A). BM Purple served as a substrate for AP and forms a blue precipitate after dephosphorylation. The results are listed in the following table and show predominant expression in invasive/migrating cells.

| Strong expression | Weak, not quite unambiguous expression |
|---|---|
| epithelial cells from endometriotic lesions | skeletal muscle |
| carcinomas | heart |
| lymphatic infiltrates | sarcomas |
| thymus | |
| germinal centers of lymph follicles (spleen) | |
| somewhat weaker: | |
| epithelial cells of the endometrium | |
| angiogenetic endothelial cells | |
| migrating nerve cells | |

Example 4

RT-PCR

RT-PCR (reverse transcription PCR) provides a sensitive method for testing the expression pattern.

For this, 1 μg of the appropriate polyA$^+$ RNA was transcribed into cDNA with the aid of 400 U of M-MLV reverse transcriptase (Gibco-BRL) in a total volume of 30 μl. 1 μl of this was employed for the subsequent PCR with different primer combinations.

The PCR primers P1 to P7 used are depicted in table 1 (see FIG. 1).

TABLE 1

Number Sequence (nucleotide position in relation to SEQ ID NO. 1

P1  5'-CCAGCTGCTGCCAAATCC-3' (36–53)
P2  5'-CATCATGGTCATAGCTGC-3' (545–562)
P3  5'-AGCGTCTCATCGGTGTAC-3' (793–776, reverse primer)
P4  5'-AACAGAAGTGGTAGGTGC-3' (1080–1063, reverse primer)
P5  5'-AAAGGGACGGGAGGAAGC-3' (1243–1260)
P6  5'-CCAAAGTAGAAAACACTG-3' (1612–1595, reverse primer)
P7  5'-GCTTGTATGACACACACG-3' (2150–2133, reverse primer)

RT-PCR experiments were carried out using polyA$^+$ RNA from different cell lines and tissues and using different primer combinations. The results are depicted in table 2.

TABLE 2

| PC | P17 | P33 | Per | EM | EJ28 | RT112 | E | EE | PEE |
|---|---|---|---|---|---|---|---|---|---|
| P1 − P4 | + | n.d. | n.d. | n.d. | n.d. | n.d. | n.d. | n.d. | n.d. |
| P2 − P6 | + | n.d. | n.d. | n.d. | n.d. | n.d. | n.d. | n.d. | n.d. |
| P5 + P7 | + | n.d. | n.d. | n.d. | n.d. | n.d. | n.d. | n.d. | n.d. |
| P5 + P6 | + | − | − | + | − | − | + | + | + |
| P1 + P3 | + | − | − | + | − | − | + | + | + |

PC = primer combination
P17 = endometriotic cell line EEC145T, passage 17, invasive
P33 = endometriotic cell line EEC145T, passage 33, noninvasive
Per = peritoneal cell line Per143T
EM = endometrial tissue
EJ28 = invasive bladder carcinoma cell line
RT112 = noninvasive bladder carcinoma cell line
E = endometrial tissue
EE = endometrial tissue of an endometriosis patient
PEE = peritoneal endometriosis biopsy
n.d. = not determined The RT-PCR results confirmed the fragment 1-specific expression in the early passages (passage 17, passage 20) of the endometriotic cell line EEC145T+. As a deviation from the Northern blot analyses it was possible to show in addition a weak expression in the endometrium.

RT-PCR analyses using intron-bridging primers

To test possible alternative exons, RT-PCR experiments using intron-bridging primers were carried out. In this connection it was possible to show at least one further mRNA species which exists alongside the mRNA described and which contains a further exon (4a) of 218 bp in length between the 4th and 5th exons. This exon is located in the 3'-UTR (untranslated region), that is to say after the coding region. The sequence of exon 4a is listed below.

gcggttgtcc ggaatgccag tggctcctgg gcagatgtgc accccagatt
   cagcctttgt gatagattcc aacacgttct ggcctcagac caccttgtg
   gtggggccag actgctctgg gcaaagtgaa gctggcctt atgctccaag
   gaagggggcc tcgagagcag gcctgcattg gctctcggac taattcgcga
   tcatctttca tacagcag Nucleotide sequence of the alternative exon 4a

Example 5

Preparation of the cDNA Phage Bank EEC14

The cDNA phage bank EEC14 was prepared according to the method of Short, J. M. et al. (1988) Nucleic Acids Res. 16: 7583–7600.

Initially, reverse transcription of polyA+ RNA from invasive cells (passage 17) of the epithelial endometriotic cell line EEC145T+ was carried out. The primer used here consists of an XhoI cleavage site and a poly(dT) sequence of 18 nucleotides in length. An adapter including an EcoRI cleavage site was ligated to the cDNA fragments produced. The two restriction sites permit directed insertion of the cDNA fragments into the ZAP Express™ vector. Inserts can be excised from the phage in the form of a kanamycin-resistant pBK CMV phagemid.

Example 6

Phage Bank Screening

The DDRT-PCR fragment 1 (394 bp) was used as a probe in order to screen $10^6$ pfu (plaque forming units) of the cDNA phage bank EEC14 according to the manufacturer's protocol (Stratagene). Labeling of the probe with digoxigenin (Boehringer Mannheim) was carried out with the aid of PCR. The plaques formed after infection of the bacterial strain XL 1blue MRF' were transferred onto a nylon membrane and hybridized thereon with the abovementioned probe. Detection of the hybridized, digoxigenin-labeled probe was carried out according to the chemiluminescence protocol by Boehringer Mannheim.

Positive plaques were selected and subjected to rescreening. The positive plaques from the rescreening were employed for the excision. Excising the vector portion from the phage by means of ExAssist helper phages resulted in kanamycin-resistant pBK CMV phagemids which could be isolated and sequenced after amplification in the bacterial strain XLOLR™. The isolated phagemid clone Q2A contained the longest insert of 2.3 kb in size whose sequence was determined and is shown SEQ ID NO. 1. The DDRT-PCR fragment 1 sequence is found as nucleotides 1235 to 1628 in relation to SEQ ID NO. 1.

Example 7

Southern Blot Analysis

10 μg of genomic DNA from female and male subjects were cleaved with various restriction endonucleases. The fragments were fractionated in an agarose gel and transferred onto a nylon membrane. Hybridization with the digoxigenin-labeled DDRT-PCR fragment 1 was carried out on this membrane.

Hybridization was detectable by chemiluminescence according to the Boehringer protocol. Using various restriction endonucleases only one band in each case was detected in both the female and male DNA samples. This result suggests that the gene on which fragment 1 is based is a single, non-sex-specific gene. Since then, two genomic clones PAC J1472 and PAC N1977 have been isolated using DDRT-PCR fragment 1.

Example 8

Fluorescence in Situ Hybridization (FISH)

The genomic clones obtained in Example 7 were localized on chromosome 1 (1p36) by means of fluorescence in situ hybridization (Lichter et al. (1990), Science 247:64–69).

Example 9

Production of Specific Antibodies

Nucleotides 584 to 909 of the abovementioned cDNA sequence were cloned by suitable restriction cleavage sites into the expression vector pMAL cRI. To express the sequence the construct was transformed into E.coli DH5 α cells. The translated protein fragment was cut out of an SDS polyacrylamide gel and employed for immunizing rabbits.

Example 10

RACE (Rapid Amplification of cDNA Ends)

Since the length of the cDNA clone Q2A (see Example 6) differs from the size of the detected mRNA (about 4 kb), RACE experiments were carried out to obtain further sequence information. With the aid of this method it is possible to obtain cDNA sequences from an mRNA template between a defined internal sequence and unknown sequences at the 5' or 3' end. The 3' end of clone Q2A could be confirmed by 3'RACE experiments starting from the 5th exon.

For the 5'RACE, first strand synthesis of the cDNA was carried out using a gene-specific primer which hybridizes in the 1st exon, and then a homopolymeric nucleotide tail was attached with the aid of the enzyme terminal transferase. This attached sequence permitted amplification of the sequence region located between the gene-specific primer and the homopolymeric nucleotide tail. This made it possible to obtain the following additional sequence which is located 5' from the Q2A sequence and belongs to the first exon:

```
cc cgg ccg ccc cga gtg gag cgg atc cac ggg cag atg cag atg cct          47
   Arg Pro Pro Arg Val Glu Arg Ile His Gly Gln Met Gln Met Pro
    1           5               10              15 cga gcc aga cgg gcc cac agg ccc cgg gac cag gcg gcc gcc ctc gtg . . .   95
Arg Ala Arg Arg Ala His Arg Pro Arg Asp Gln Ala Ala Ala Leu Val . . .
            20              25              30
```

The underlined sequence represents the first nucleotides of the Q2A sequence, the sequence in front of it corresponds to the novel sequence obtained by 5' RACE. The open reading frame fits into the one already derived for fragment and contains two putative start codons (underlined).

The nucleotide sequence which has the sequence previously obtained and is depicted in SEQ ID NO. 1 and the additional 84 nt at the 5' end is depicted in SEQ ID NO. 3.

Example 11

Cellular Localisation of the Frag-1 Protein

By means of computer-based analyses of the almost complete frag-1 cDNA an open reading frame could be detected coding for a protein having a total length of 411 amino acids. A further computer-based analysis of the amino acid sequence showed a significant outside→inside transmembrane domain within the protein, as well as a somewhat unusual signal peptide sequence comprising the amino acids 1–43. This fact renders it probable that frag-1 could be a transmembrane protein.

The localisation of the frag-1 protein should, on the one hand, be performed by means of a birch profiline (BP)-tag and, on the other hand, as GFP (green fluorescent protein)-fusion protein. For this purpose the sequence coding for frag-1 was first cloned into a pcDNA3.1-vector (in-vitrogen, Leiden, Netherlands), which had already been furnished with the sequence of the birch profiline-tag. This frag-1-BP-vector was inserted into different eukaryotic cells by means of SuperFect (company Qiagen). About 40 h after transfection the cells were fixed with 4% paraformaldehyde, permeabilized with 0.2% of Triton X-100 and the frag-1 protein (frag-1 BP) tagged by the C-terminus was detected by means of a BP-specific antibody.

For the production of the frag-1-GFP fusion protein the commercially available vector pEGFP-N3 (Clontech, Heidelberg) was selected, which allows an expression of GFP at the C-terminus of frag-1. The complete coding sequence of frag-1 was also cloned into this vector, so that in the end a fusion protein develops consisting of the frag-1 protein having a length of 411 amino acids, at the C-terminus of which the GFP-protein is situated (frag-1-GFP). With the aid of this construct the expression was examined in the same eukaryotic cells as with the aid of the frag-1 protein tagged with BP. Approximately 40 h after SuperFect-transfection the cells were also fixed with 4% paraformaldehyde, washed with PBS and evaluated directly in the fluorescence-microscope. The preliminary result for the tested cell lines EEC145T+, 12Z (both epithelial endometriotic cell lines) and MCF-7 (mamma carcinoma-cells) can be described as follows:

MCF-7

Those cells are mamma carcinoma-cells growing in typical epithelial cell associations due to their E-cadherin-expression and exhibiting the compact cell form characteristic of epithelial cells. Since these cells express frag-1 and, thus, possess the cellular background for a physiological frag-1 expression, and, furthermore, rather possess epithelial cell character as compared to the endometriotic cell lines in culture, they were selected for first expression studies. In this context, it turned out that the expression patterns of the constructs explained above (frag-1-BP and frag-1-GFP) differ from one another. Whereas frag-1-BP for the most part gets stuck in the Golgi's apparatus, the frag-1-GFP also occurs in the cell membrane. The distribution into the two cell compartments, however, depends on the strength of expression of frag-1-GFP.

EEC145T+

This cell line has already been described several times and served as starting point for the frag-1 isolation. For this reason it was interesting to examine the localisation in these E-cadherin-negative cells of epithelial origin. As compared to MCF-7 these cells do not exhibit the typical epithelial appearance, but rather possess a fibroblastoid growth behavior. In this respect, differences in the expression of both examined constructs, frag-1-BP and frag-1-GFR, can be noticed as well, membrane discolorations being again noticeable with both constructs. In this context, in cells expressing frag-1-BP a significant accumulation of the fusion protein in the Golgi's apparatus can be detected as well.

If frag-1 is actually a transmembrane protein which follows the typical synthesis route via endoplasmatic reticulum (ER) and Golgi's apparatus, an accumulation of overexpressed, not yet completely processed frag-1 protein in the Golgi's complex can easily be explained.

12Z

This cell line is also an epithelial endometriotic cell line, which was obtained by transfection of the SV40 T-antigen, and is, just like EEC145T+, E-cadherin-negative. These cells exhibit in culture a similar pattern of growth as EEC145T+, and, thus, were selected as second endometriotic cell culture system for controlling the frag-1 expression. The results of the frag-1-BP and frag-1-GFP expression obtained so far correspond to the results described above for the cell line EEC145T+.

Example 12

Expression Profile of Fragment-1-mRNA by Means of in Situ-hybridization

When preparing the expression profile of fragment-1-mRNA the method of in situ-hybridization was selected. This method renders possible to visualize the localisation of nucleic acids in tissues, cells and nuclei or chromosomes in vivo with the aid of labeled control probes. In this manner the spatial as well as the temporal expression pattern of various genes can be obtained and depicted. The advantage of this method, thus, consists in the detection of the mRNA to be found on the cellular level within a tissue association.

When determining the fragment-1 expression in various human tissue samples biochemically labeled RNA-probes (ribo probes) were used. The respective probe models were cloned within a vector having promoter sequences of bacteriophage-RNA-polymerases (e.g. Bluescript vectors by Stratagene with T3/T7-RNA-promoters). When producing the probes the probe models were linearized with a restriction endonuclease. Subsequent to the phenol/chloroform-extraction the sense- and antisense-ribo probes were produced by using the corresponding RNA-polymerases by means of in vitro-transcription, and thereby being marked with digoxigenin. In order to be able to hybridize the tissue samples with these produced ribo probes, the tissue first has to be freed from paraffin and to be hydrated in a declining ethanol series. Afterwards the preparations are pre-treated with several solutions and permeabilized thereby. Subsequently, the preparations are hybridized with the produced ribo probes overnight. For the immune-histochemical detection of the hybridized digoxigenin-labeled ribo probes anti-digoxigenin fab-fragments with conjugated alkaline phosphatase were employed. As substrate for this alkaline phosphatase BM Purple AP-substrate was employed resulting in a blue color-precipitate. The color reactions each pair of probes (sense- and antisense-ribo probes) were always started simultaneously and stopped as soon as the blue coloring of the sense-ribo probe started.

By means of using different control probes the in situ-hybridization could be established and standardized during its course. Additionally, the hybridization results of these control probes furnished further information about the composition of the tissue. With the aid of a digoxigenin-labeled antisense-ribo probe of the DDRT-PCR-fragment-1 the various human tissue samples were examined as to their fragment-1 expression within the tissue association. In this connection a hybridization could be detected within the large intestine, embryo, endometrium (3 samples), endometriosis (3 samples), spleen, ovaries (2 samples), pancreas, placenta, prostate and thymus. Within these tissues the fragment-1-mRNA is primarily expressed within the epithelial cells, can, however, also be detected in migrating nerv cells, angiogenetic endothelial cells, lymphocytes as well as decidua and ovarian stromata. The increased fragment-1-mRNA expression in the endometriotic glands strikingly differs from the one in the endometrial glands. This increased expression can also be detected in carcinomas (10 samples) and sarcomas (3 samples). This increased expression is less detectable within the sarcomas. The sarcomas are malign soft-tissue tumors that are classified according to the departing mother tissue. Contrary thereto, a hybridization could not be detected within granular tissue, liver, lung and the thyroid gland.

TABLE 3

Cell type-related expression chart of fragment-1

| epithelial cells | other cells |
| --- | --- |
| chorio-epithelium | decidua |
| large intestine cavities | germinal centers of the |
| embryonic epithelials | lymphatic follicles (spleen) |
| endametrial glands | lymphatic infiltrates |
| endometriotic glands | satellite cells (spleen) |
| endothelial cells, | nerv cells, migrating |
| angiogenetic carcinomas | ovarian stromata |
| pancreas glands | sarcomas |
| prostate glands | |
| tubal epithelium | |
| thymic epitheliocytes | |

As can be seen from these data, fragment-1 is mainly expressed in epithelial cells as well as in cells having an invasion or rather migration potential. Fragment-1 is particularly expressed in the carcinomatous areas of the liver and lung, although these tissues do not ordinarily express the fragment-1-mRNA. The liver contains the metastasis of a colonic carcinoma and the lung a papillary adenocarcinoma.

| DDRT-PCR- Fragment 1 (394 bp) | | | | |
| --- | --- | --- | --- | --- |
| 479 bp E1 | 90 bp E2 | 245 bp E3 | 133 bp E4 | 1253 bp E5 |
| → P1 | → P2 | ← P3 | ← P4 | → P5  ← P6  ← P7 |

E1–E5: Exon 1 to Exon 5
The respective exon sizes are indicated above the drawing.
P1–P7: PCR primer
For sequences and exact identity of the primers see table 1
The position of the DDRT-PCR fragment 1 sequence is indicated by a black bar.

What is claimed is:

1. A polypeptide associated with invasive processes in endometriosis, wherein said polypeptide is encoded by a nucleic acid comprising
   (a) the nucleotide sequences depicted in SEQ ID NO:1, 3 or/and 5, a combination or a protein-encoding segment thereof,
   (b) a nucleotide sequence corresponding to the sequence in (a) within the scope of the degeneracy of the genetic code, or
   (c) a nucleotide sequence hybridizing with the sequences in (a) and/or (b) under stringent conditions of washing for one hour with 1×SSC and 0.1% SDS at 50° C.,
   wherein the polypeptide encoded by the nucleic acid comprising the nucleotide sequence depicted in SEQ ID NO:1 or 3 in (a) is substantially isolated.

2. A polypeptide associated with invasive processes in endometriosis, said polypeptide comprising
   (a) an amino acid sequence depicted in SEQ ID NO: 2 or 4, or
   (b) a homology of more than 90% to the amino acid sequence according to (a),
   wherein the polypeptide in (a) is substantially isolated.

3. A polypeptide comprising an amino acid sequence according to claim 1, with at least one modification so that a biological and/or immunological activity is substantially preserved.

4. A peptide comprising a segment of at least 10 amino acids of the amino acid sequence depicted in SEQ ID NO: 2 or 4.

5. A composition suitable for the diagnosis of endometriosis, comprising as an active component admixed with a carrier, excipient and/or additive, wherein the active component is selected from the group consisting of a polypeptide according to claim 1, 2 or 3, and a peptide according to claim 4.

6. A composition according to claim 5, wherein the carrier, excipient and/or additive is pharmaceutically conventional.

* * * * *